(12) United States Patent
Brenner

(10) Patent No.: US 7,200,348 B2
(45) Date of Patent: Apr. 3, 2007

(54) VOLATILE ORGANIC COMPOUND DETECTOR

(75) Inventor: Robert E. Brenner, New Richmond, WI (US)

(73) Assignee: Samsung Electronics Co., Ltd, Suwon, Kyungki-Do (KR)

( * ) Notice: Subject to any disclaimer, the term of this patent is extended or adjusted under 35 U.S.C. 154(b) by 304 days.

(21) Appl. No.: 10/879,895

(22) Filed: Jun. 29, 2004

(65) Prior Publication Data

US 2005/0286927 A1    Dec. 29, 2005

(51) Int. Cl.
*G03G 21/00* (2006.01)
(52) U.S. Cl. .......................................... 399/91; 399/93
(58) Field of Classification Search ............ 399/91–93, 399/250
See application file for complete search history.

(56) References Cited

U.S. PATENT DOCUMENTS

| | | | | |
|---|---|---|---|---|
| 3,890,721 A | * | 6/1975 | Katayama et al. ............. | 34/73 |
| 4,254,195 A | * | 3/1981 | Hara et al. ..................... | 430/17 |
| 5,331,287 A | | 7/1994 | Yamagishi et al. .......... | 324/724 |
| 6,512,900 B2 | * | 1/2003 | Sakai ........................... | 399/93 |
| 6,744,996 B2 | | 6/2004 | Brenner ....................... | 399/57 |
| 2004/0047646 A1 | | 3/2004 | Yon et al. ..................... | 399/93 |

FOREIGN PATENT DOCUMENTS

| | | |
|---|---|---|
| EP | 0 596 973 | 12/1995 |
| JP | 03116166 A * | 5/1991 |

* cited by examiner

*Primary Examiner*—David M. Gray
*Assistant Examiner*—Ryan Gleitz
(74) *Attorney, Agent, or Firm*—Mark A Litman & Associates, P.A.

(57) ABSTRACT

A printer system using inks, toners or developers with solvents therein is provided with a detector for volatile organic compounds assists in reducing potential accidents in the printer. The detector may be able to identify at least a threshold level of volatile organic in a gas phase in the printer, or may be able to identify various levels or a continuous metered level of volatile organic compounds (VOC's). An automatic warning, automatic signal, or even automatic cutoff function may be associated with the detector. The detector may be inside the printer or associated with a vent or generally positioned on or near the printer. One mode of detection operation described in detail is identification of changes in dielectric constant in a vapor phase or vapor stream that can be associated with changed levels of VOC in that phase or stream.

16 Claims, 3 Drawing Sheets

VOLATILE ORGANIC COMPOUND DETECTOR

BACKGROUND OF THE INVENTION

1. Field of the Invention

The present invention relates generally to sensors for volatile compounds in the gas phase, and to sensitive sensors for sensing the presence of target volatile organic compounds contained in fugitive emissions, for example in the environment where inks, toners, and volatiles are generated in imaging processes.

2. Description of Related Art

There is an ever-increasing desire to reduce gaseous emissions from industrial sources, given the environmental and health threats such emissions may pose. Most of the industrial air pollutant emissions are generated by two types of companies, namely chemical manufacturing companies and oil refineries. Emissions from these types of industries are of two basic types: (1) stack gas emissions, and (2) fugitive emissions (i.e., leaks), the latter of which represent about one-half of the total emissions. Therefore, a major decrease in total emissions from these industrial sources will require a significant reduction of fugitive emissions. Of greater local interest tends to be emissions in buildings or rooms where concentration of emissions may tend to be high. It is has been found that offices can readily exceed safety standards for volatile organic compounds because of the large use of printers and copiers. These imaging systems generate volatile solvents whenever liquid inks, toners or developers are used.

Originally, personnel would smell out issues of excess environmental solvents (which some would say exists when any solvent is present in the ambient office space). The detection could be done by direct smell detection by employees or with sniffers carried through the office. These devices would be chemical sensors that could be carried by hand as employees walk through facilities. An old-fashioned hand-held sniffer typically consisted of a long tube through which air samples are drawn to reach a flame ionization detector component.

A problem with the use of sniffers for leak detection is that this method does not provide continuous, around-the-clock monitoring. Human smell detection suffers from too ready detection saturation, wherein the person's olfactory senses lose their ability to recognize an odor to which they are regularly exposed over long periods of time.

The detection of volatile compounds in gaseous emissions include the detection of pollutants (such as hydrocarbons, aromatics, and the like) in what has been referred to as "office exhaust" from copiers and printers, and is a potentially significant health issue. Sensors for these office spaces would require sensors with increased sensitivities over those used to detect fugitive chemical plant emissions. Specifically, sensors to be used in the ambient air in which target vapors are greatly diluted with air may require sensitivities of at 100 ppm and less, and often in the sub-ppm regime.

An inexpensive sensor that may be easily and flexibly employed in chemical plant environments to continuously monitor fugitive emissions is disclosed in U.S. Pat. No. 5,417,100, entitled "Reversible Sensor for Detecting Solvent Vapors." Specifically, this patent discloses a fugitive emissions sensor for reversibly detecting solvent vapors that comprises a pair of electrically-conductive interdigitated electrodes disposed on the surface of a dielectric substrate and a composite coating covering the interdigitated electrodes comprising (1) a conductive polymer having a conductivity within the range of about $10^{-6}$ to 1 S/cm, and (2) a dielectric polymer with an affinity for the solvent vapors of interest. The dielectric polymer is the major component of the composite coating and serves as an attractant for the targeted solvent vapor. The ratio of conductive polymer to dielectric polymer is about 1:1 to 1:5. It is contemplated that readings from such sensors would be monitored and recorded by a computer, which would then notify operators of the occurrence and location of any detected leaks.

It is known to use conductive polymers as the active material in sensors for detecting a variety of compounds, such as acids, alcohols, complex metal ions, and proteins. Stable conductive polymers include polypyrrole, polythiophene, and polyaniline (PANi); such materials may be readily modified by the attachment of particular functional groups and/or the incorporation of appropriate counterions during synthesis in order to detect, by selective interaction, specific compounds. Conductive polymer sensors are advantageous because they are compact, simple, inexpensive, and easy to make.

Another monitoring device using conductive polymers is known which indicates the presence of acid. This device is disclosed in U.S. Pat. No. 5,331,287, entitled "Device and Method for Sensing Water and/or Acid in the Presence of Water in Non-Aqueous Media." Specifically, a sensor is disclosed therein for monitoring the water and acid content that is particularly suited for monitoring the quality of nonaqueous fluids in equipment or vehicles. The sensor comprises an insulating substrate, interdigitated electrodes formed on the substrate, and a conductive polymer deposited over the interdigitated electrodes that bridges between adjacent digits thereof. The conductive polymer reversibly increases conductivity in measurable amounts with increasing acid and/or water content due to protonation by the acid or hydration by the water.

European Patent Application 596,973, entitled "Device for Sensing Volatile Materials" discloses a device for sensing volatile material in the gas phase comprising a pair of electrical contacts with a semi-conductive polymer extending between the contacts. A charge balance in the polymers is achieved using counterions in a proportion of about one counterion to four monomer units. Typical polymers used include polypyrrole, poly-N-methylpyrrole, poly-3-methylthiophene, polyaniline, poly-5-carboxyindole, poly-3-methyl-phenylamine, polybithiophene, polythiophene, poly-3-thiopheneacetic acid, and polyfuran. Typical counter-ions that may be used to synthesize the polymers may be tetrafluoroborate, alkyl sulfonates, tetramethylamimonium chloride, chlorates, and perchlorates. The sensors are used in the form of an array to develop a fingerprint of a particular "odor." Specifically, the reference teaches the use of an array of eleven sensors to distinguish between different brands of lager beer and between two samples of the same beer that had been stored differently.

The issue of volatile organic compounds within developing systems (e.g., printers) is an obviously dangerous situation, with combustible or flammable vapors airborne in an electrical environment. Published U.S. patent application Ser. No. 20040047646 describes a wet-type electrophotographic printer having a printer body. The printer comprises a discharge passage through which air inside the printer body is discharged out to an outside of the printer body, at least one discharge fan positioned inside the discharge passage to guide the air inside the printer body to the outside of the printer body, and a photocatalystic filter positioned inside the discharge passage, and having a photocatalystic body coated with a photocatalyst, a plasma electrode disposed on the photocatalystic body, and a plasma generator coupled to the plasma electrode to filter and deodorize the air inside the printer body. This construction assists in reducing room odor. Published U.S. patent application Ser. No. 20040047646 and U.S. Pat. No. 6,744,996 are hereby incorporated by reference in their entirety.

SUMMARY OF THE INVENTION

A printer system using inks, toners or developers with solvents therein is provided with a detector for volatile organic compounds assists in reducing potential accidents in the printer. The detector may be able to identify at least a threshold level of volatile organic in a gas phase in the printer, or may be able to identify various levels or a continuous metered level of volatile organic compounds (VOC's). An automatic warning, automatic signal, or even automatic cutoff function may be associated with the detector. The detector may be inside the printer or associated with a vent or generally positioned on or near the printer. One mode of detection operation described in detail is identification of changes in dielectric constant in a vapor phase or vapor stream that can be associated with changed levels of VOC in that phase or stream. Air has a dielectric constant of 1.0 and the Norpar® carrier vapor (hydrocarbon emissions) has a dielectric constant of 2.01. The sensor provides a constant monitor for the dielectric constant of the atmosphere inside the printer (or alternatively, or additionally the dielectric constant of the printer emissions that are leaving the catalyst) and acts to disable the machine if the concentration reaches a predetermined threshold.

DETAILED DESCRIPTION OF THE INVENTION

Figure 1:
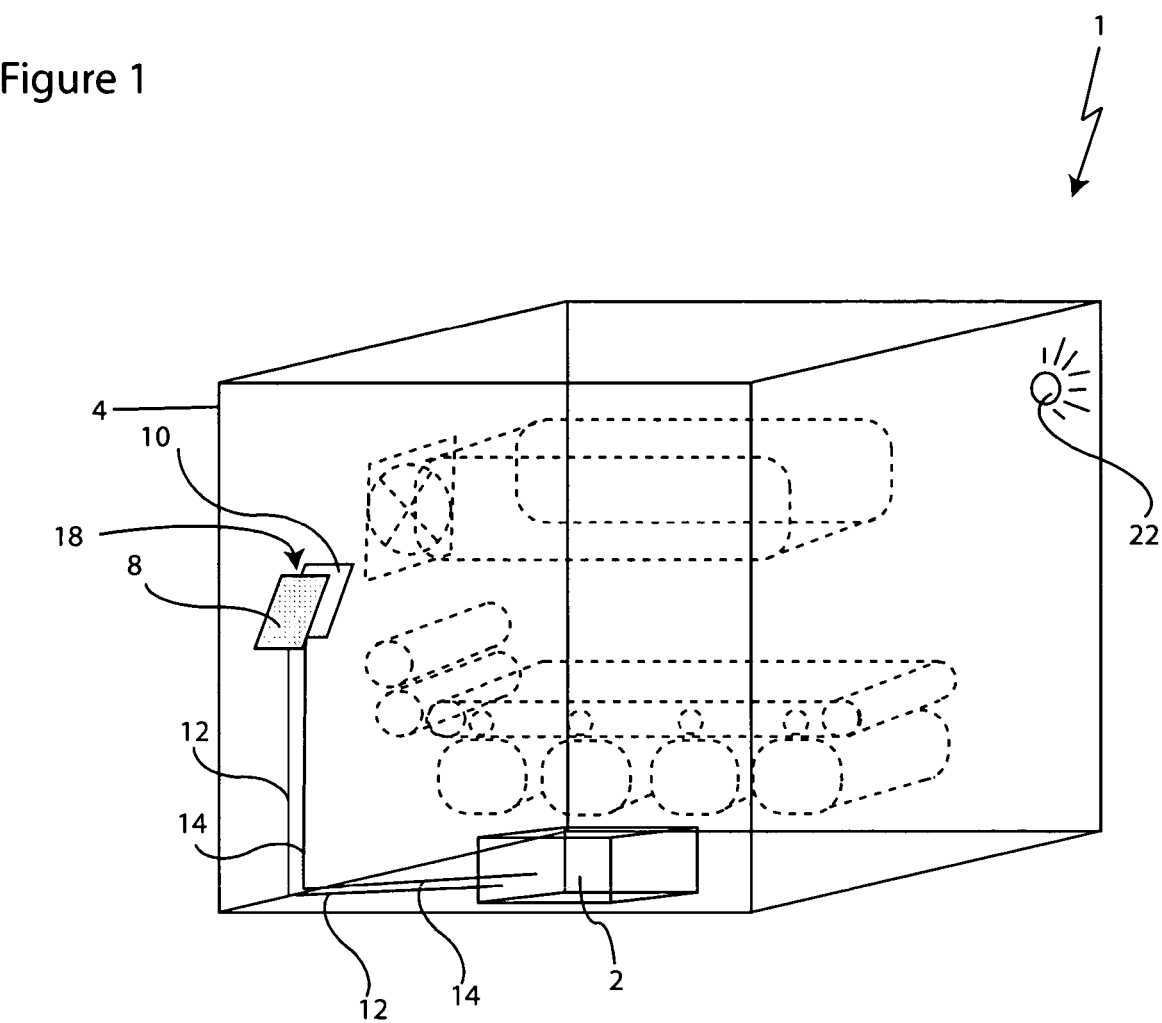
FIG. 1 shows a circuit design that can provide dielectric measurement data in a printer to identify changes in VOC concentration.

Electrophotographic printing systems are well known in the commercial and industrial markets. In their simplest terms, they are units that produce a differential electrostatic charge image (in the electrophotographic field, this can be referred to as a latent image or latent charge image) on a substrate (e.g., photoreceptive drum, belt, sheets); the substrate with an electrostatic charge image thereon is subsequently exposed to an environment with an ink (e.g., liquid ink, toner, or developer in droplet form; or, in dry electrophotography, a powder), which is differentially attracted to areas of the substrate with differential charging thereon. The ink forms an intermediate (not yet permanent) image on the latent electrophotographic charge image, then the intermediate image is subsequently transferred to a final substrate (e.g. paper, transparency film, etc.) and affixed by heating, irradiation, drying, fusing or any other stabilizing mechanism. Alternatively, an intermediate transfer member may carry the intermediate image from the initial substrate (photoreceptive element) to the final substrate.

The inks (particularly liquid inks, toners or developers) may have carrier liquids and/or solvents present in the ink. A very common form of carrier liquid is an inert and/or charge neutral, non-polar carrier liquid such as a hydrocarbon oil. These are sold under many different tradenames such as Norpar®, Isopar®, and Exxsol®. The inks also contain colorant material, polymers, stabilizers, charge acceptors or charge directors, antioxidants, and other adjuvant materials. When the image is stabilized (e.g., by drying, fusing, curing or polymerizing, etc.), volatile materials are driven from the ink that has been deposited on the substrate as the carrier liquid evaporates.

Many of the printers will have a venting system to vent airborne volatiles removed from the ink to the ambient environment where the printer is located. Very often the airborne volatiles in the ink are passed through a carbon adsorbent or a heated catalyst to remove the harmful components or oxidize them into less harmful sub-components. Sometimes ambient dissipation or ambient room venting is relied upon in an attempt to assure that the volatile organic compounds are removed from the printer and the printer environment. There are many factors that can lead to a sudden rise in the airborne concentration of volatile organic compounds within a printer. A non-limiting list of theoretic causes of increased VOC vapor concentration within a printer are included clogged venting system, underperformance of fan in venting system, improper positioning of printer vents (e.g., against a wall), excess ink delivery, spurious buildup of hydrocarbon deposits within a printer that are vaporized later during an imaging process, catalyst failure, or failure of an adsorbent bed to be regenerated and the like. The cause of the excess VOC buildup is less important than the fact that VOC levels can increase to dangerous levels in printers without any way of a user appreciating the problem, except for a catastrophic breakdown of the printer.

The use of a sensor in a position that can detect VOC concentration buildups around and particularly in a printer is a desirable safety feature. The means of detection can be any means that provides an observable signal or an electrical that can be used to provide or initiate an observable or recordable signal. There are many known ways of detecting gases that can provide this function, such as the use of diodes or semiconductors that change their electroluminescence or reflectance, or absorption, or luminescence when a concentration of gas contacts an active surface of the device. Such detection elements are shown, by way of non-limiting examples, in U.S. Pat. Nos. 4,364,995; 4,645,932; 4,752,588; 4,780,643. Acoustic wave device chemical sensors may be used, such as those shown, by way of non-limiting example, in U.S. Pat. Nos. 6,432,362; and 6,237,397.

Circuitry that measures electrical property changes in the ambient or contained air phase or gas streams in the printer which can be used to relate the changes to increased or altered VOC content in the phase or stream can also be used. As the chemical nature of the volatiles that are available to be added to the phase or stream are known (that is, the manufacturer of the printer usually provides the inks and therefore knows the VOC ingredients in the ink), the electrical effects of those specific VOC's in a phase or stream can be predicted with a high degree of certainty. Measurements of the resistance, conductance and/or dielectric properties of the phase or stream can be produced, and those properties can be correlated to a database or look-up table (physical or electronic) to determine what the VOC concentration is in the phase or stream. For example, air has a dielectric constant of 1.0 and the Norpar® carrier vapor (hydrocarbon emissions) has a dielectric constant of 2.01. The sensor of the present invention may provide a constant monitor for the dielectric constant of the atmosphere inside the printer (or alternatively, or additionally the dielectric constant of the printer emissions that are leaving the catalyst) and acts to disable the machine if the concentration reaches a predetermined threshold. Threshold levels can be identified as important concentrations, and signals generated (e.g., lights, sounds, electronic signals, automatic shut-offs, etc.) when specific or general threshold measurements have been made.

A method for determining the concentration of VOC materials in a phase or stream is described. One embodiment involves a series of steps. An electrical signal generator is electrically connected to a first electrode. A second electrode, attached or electrically connected to a detecting device, is positioned at a prescribed gap distance (e.g., between 0.005 inches and 0.250 inches) from the first electrode. The two electrodes are submerged in the phase or stream (in one practice of the invention in an electrophotographic imaging system, within the printer housing), maintaining the prescribed gap distance from one another. The signal generator then transmits an alternating current electrical signal (AC signal) or a direct current signal (DC signal) having a known amplitude to the first electrode. The direct current signal may be pulsed, and the receiving/signaling system may respond to the onset or lack of pulses over a period of time to provide a base point for indicating the electrical properties of the phase or stream. The second electrode then receives any residual signal that is transmitted or propagates across the prescribed gap distance. The amplitude of the received signal is either detected at an acceptable intensity or determined to be absent or below the acceptable level, and a warning may be generating based on whether the signal is received at the acceptable level or not received at an acceptable level (the unacceptable level including no signal received). Additionally, decisions may be made based on the amplitude of the received signal.

In one embodiment, the signal generator's output is, by way of a non-limiting example, between about 0.05 and 50 MHz; between 0.1 and 10 MHz, e.g., between 0.5 and 5 MHz, such as at 1 MHz. Signal frequency below 10 MHz, below 5 MHZ, or below 1 MHz can be used easily and desirably. In an of the method, the first and second electrical emitting and electrical sensing elements, e.g., the probes are between 0.01 and 0.06 inches, between 0.01 and 0.03; between 0.01 and 0.045, or between 0.035 inches and 0.045 inches apart.

There are various possible embodiments and ways to position the detection device element that may be used to send the warning signal that a predetermined level of VOC concentration has been reached. In the most basic embodiment, there is an electrical path in a simple series connection with the sensing device. When the VOC vapor to be detected has a dielectric constant below that of the ambient air, as the concentration of harmful vapor increases, the concentration of ambient air will decrease. In such a case, the gas in the gap between the electrodes will be more conductive and the electrical signal will be transmitted strongly across the gap. At this point, the AC signal may be strong enough to light a warning light, or trigger a system to disable the printer. When the VOC vapor to be detected has a dielectric constant above that of air, the conductivity of the gas in the gap will decrease and the strength of the signal reaching the second electrode will be decreased. When insufficient current is received at the second electrode, the electrical series connection is broken and a light, LED, or other signaling device ceases to relay a message to a receiver or fails to provide a visual signal that the threshold condition has been reached or has not been reached. In this embodiment, the absence of the signal to an observer is the warning indicator or the absence of the internal light signal may trigger a second signaling feature to engage to provide a visible light signal. When the sensor(s) have an indication that levels of VOC's are in excess of a predetermined level (which may be an industry standard, EPA level, or in case of internal readings, manufacturer suggested maximum levels for health and/or safety reasons), a signal is preferably provided; more preferably an automatic cutoff for the device is provided to shut down the equipment. If alphanumeric information can be provided by logic or processor associated with the machine, a written indication of the problem that led to the shutdown would be desirable.

In another embodiment, the AC signal is converted to an analog signal and can be read, interpreted or processed by such devices as meters, processors, and the like. In such an embodiment, the percentage of VOC materials in the phase or stream in a printer may be accurately determined at any given time.

The described technology includes a method for determining the percentage of VOC material in a phase or stream, either in scholastic units (that is arbitrary units that indicate a state of acceptability or non-acceptability, such as 1–10) or actual concentration units (e.g., ppm, parts per million) in the phase or stream. For example, the dielectric constant of air is 1.0 while the dielectric constant of a particularly useful hydrocarbon vapor is about 2.01. The precise dielectric constant is not important so long as it is sufficiently different from that of air so that significant variations in concentrations can be determined by commercially available data. Variations of +0.1 in direletric constants (e.g., $\leq 0.90$ and $\geq 1.1$) would be a reasonable, non-limiting example, of the range of dielectric properties that could be easily measured in VOC materials used with the practice of this technology. It would be possible to measure the dielectric constant using a range of 1.0 to 2.01, or it might be preferred to assign the dielectric constant of air (1.0) a number, 1, while the dielectric constant of the hydrocarbon to be detected (2.01) could be assigned a number, such as 10. A method may, for example, comprise the steps of providing an electrical signal generator on the printer providing a first electrode electrically connected to the signal generator, the first electrode submerged in the phase or stream, providing a second electrode at a predetermined gap distance from the first electrode, the second electrode submerged in the phase or stream which might contain VOC emissions from the ink and connected to an electrical signal detector, transmitting an alternating current signal having an amplitude from the signal generator to the first electrode, detecting the AC signal, a change in the AC signal or its absence with the electrical signal detector, determining the amplitude, rate of change, degree of change or absence of the AC signal at the second electrode, and generating a high VOC warning signal in response to the amplitude being detected at the second electrode at an amplitude below a predetermined minimum level. The second electrode may be, by way of non-limiting examples, between 0.001 inches and 0.250 inches from the first electrode. The method may provide an indicator light that stays on in response to sufficient amplitude, and goes out in response to insufficient amplitude when the alternating or direct current signal is detected and its amplitude determined. The alternating current signal may be picked up at the second electrode by a detecting device which converts the alternating current signal to an analog signal. The resultant analog signal may be sent to a processor for conversion or translation into a warning indication for the user.

For the purposes of this description, certain terms will have the following meanings:

Electrode—an electric conductor through which an electric current enters or leaves a medium, whether it be an electrolytic solution, liquid, gas, solid, molten mass, or vacuum. (Taken from McGraw-Hill Dictionary of Scientific and Technical Terms, 4.sup.th Ed. 1989).

In FIG. 1, a printer configuration 1 comprises a signal generator 2 that supplies an electrical signal (e.g., by way of non-limiting example, an AC signal) having a known amplitude (in this example, via a wire 12) to a first electrode 8 that is submerged in a housing of a printer 4 that may contain VOC's produced by deposition or stabilizing ink from a liquid image developer (shown only as dashed lines). A second electrode 10 is positioned between 0.001 and 0.250 inches from the first probe 8 to create a gap 18. A gas phase or gas stream is permitted to flow in the gap 18. The second electrode 10 is connected to a detector 16 which may be, by way of non-limiting example, as simple as a light bulb 22 in series (not shown) with the electrical signal path from the electrical signal generator, or which may include, for example, such components as an amplifier and/or rectifier, converter, chip, or microprocessing component (contained in processing unit 2). As the AC electrical signal sent through the first electrode 8 reaches the gap 18, it is conducted across the gap 18 to the second electrode 10 by conductive components in the gas phase or gas stream. If the concentration of VOC's in the phase or stream is within minimal (acceptable) limits (e.g., a sufficiently low concentration), the AC signal is more fully conducted or at least conducted to a minimally required level, and the amplitude of the AC signal closely approximates that of the generated signal or is maintained at a sufficiently high level as to indicate the presence of sufficiently low concentrations of VOC's in the phase or stream. As the concentration of VOC material in the phase or stream increases (these materials are non-polar in general, and so are less conductive than air), the resistance in the gap increases and less of the AC signal reaches the second electrode and detector. As the amplitude received by the detector decreases to below a "trigger point" or pre-determined minimum level, a signal may be generated (including even the light emitting element or bulb failing to be lit) to indicate to the user that the VOC concentration is no longer acceptable for safe printing conditions.

Figure 2:
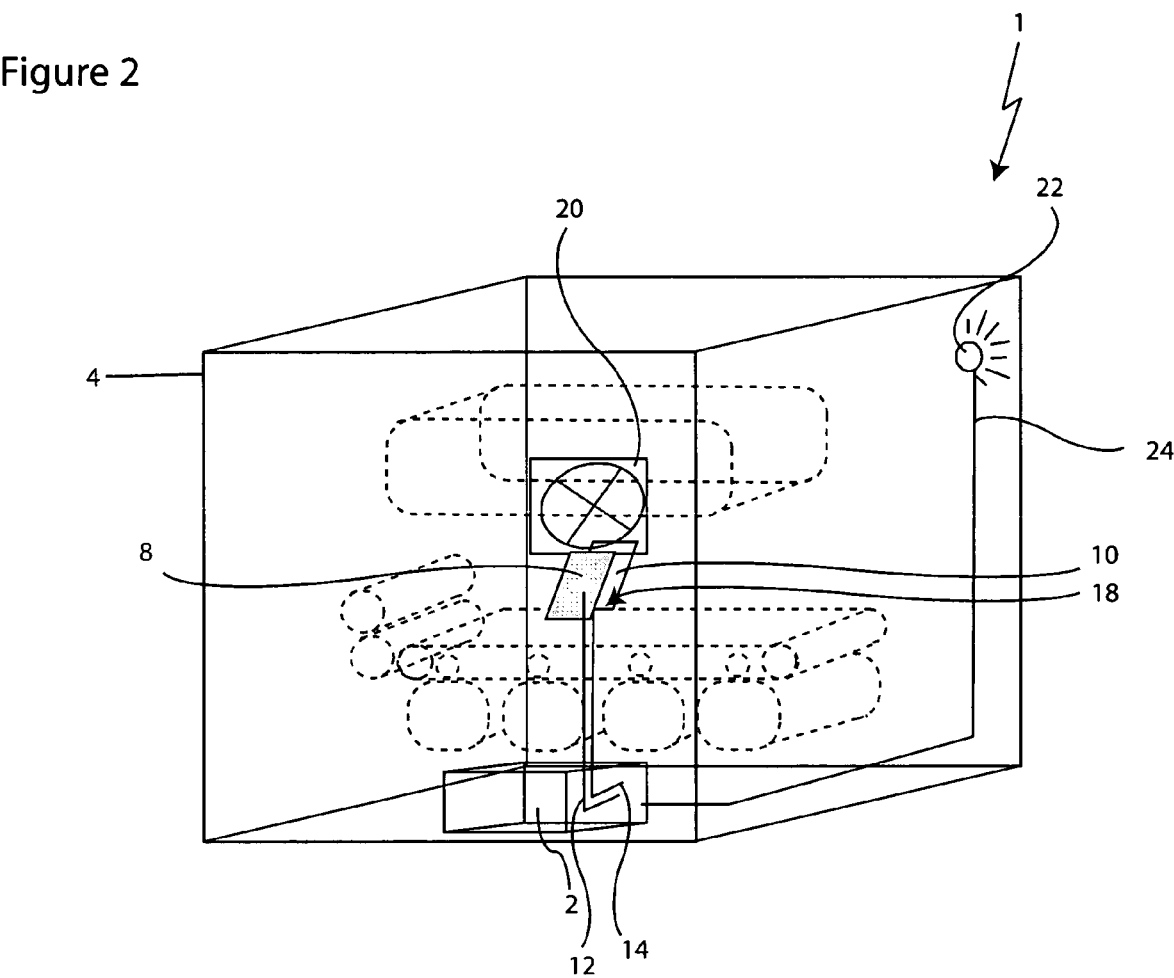
FIG. 2 shows a detector positioned immediately adjacent a vent on an electrophotographic printer.

FIG. 2 shows a printer configuration 1 (printer parts not included in this invention are designated by dotted lines) having the sensor of the present invention located external to the printer housing 4, at an exhaust port 20 that may or may not have a fan or other air movement mechanism. A signal generator 2 supplies an electrical signal (e.g., by way of non-limiting example, an AC signal) having a known amplitude (in this example, via a wire 12) to a first electrode 8 that is mounted at an exhaust port on the housing of a printer 4 that may contain VOC's produced by deposition or stabilizing ink from a liquid image developer unit or hydrocarbon vapor processing unit (shown only in dashed lines as they may form countless embodiments). A second electrode 10 is positioned between 0.001 and 0.250 inches from the first probe 8 to create a gap 18. A gas phase or gas stream is permitted to flow in the gap 18. The second electrode 10 is connected to a detector 16 which may be, by way of non-limiting example, as simple as a light bulb 22 in series (not shown) with the electrical signal path from the electrical signal generator, or which may include, for example, such components as an amplifier and/or rectifier, converter, chip, or microprocessing component (which may be contained in processing unit 2). As the AC electrical signal sent through the first electrode 8 reaches the gap 18, it is conducted across the gap 18 to the second electrode 10 by conductive components in the gas phase or gas stream. If the concentration of VOC's in the phase or stream is within minimal (acceptable) limits (e.g., a sufficiently low concentration), the AC signal is more fully conducted or at least conducted to a minimally required level, and the amplitude of the AC signal closely approximates that of the generated signal or is maintained at a sufficiently high level as to indicate the presence of sufficiently low concentrations of VOC's in the phase or stream. As the concentration of VOC material in the phase or stream increases (these materials are non-polar in general, and so are less conductive than air), the dielectric constant of the gas in the gap 18 increases and the electrical resistance in the gap increases and less of the AC signal reaches the second electrode and detector. As the amplitude received by the detector decreases to below a "trigger point" or pre-determined minimum level, a signal may be generated (including even the light emitting element or bulb failing to be lit) to indicate to the user that the VOC concentration is no longer acceptable for safe printing conditions.

In a very basic embodiment, the detector can be a simple light bulb 22, for example. As long as the AC signal is sufficient to light the bulb, the low concentration of solid conductive particles within the phase or stream is satisfactory. If the VOC material would increase the conductivity, the presence of excess VOC would be indicated by an increase in conductance. When the bulb is no longer illuminated, not enough of the AC signal is crossing the gap because of the presence of sufficiently high concentration of VOC, and the printer should be examined or turned off. The turnoff function may be automatic.

A more complex embodiment utilizes more sophisticated hardware to detect the amplitude of the signal received at the second electrode. Hardware such as amplifiers, rectifiers, converters, chips, and microprocessors (or even a simple meter or look-up table) can all be additional steps that evaluate, measure, break down, or process, the signal received at the second electrode and help the user determine when to inspect, moderate, shut down, or otherwise examine or alter the printer or its condition. These additional steps and hardware inclusions are virtually limitless and are not necessary, although to individual designers they may be preferred, for the function of the present technology.

Figure 3:
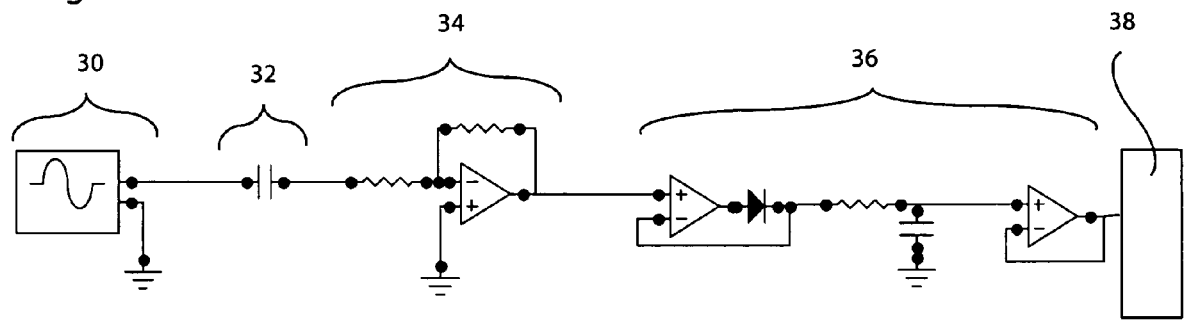
FIG. 3 shows the circuit design of FIGS. 1 and 2 as an electrical diagram.
Figure 4:
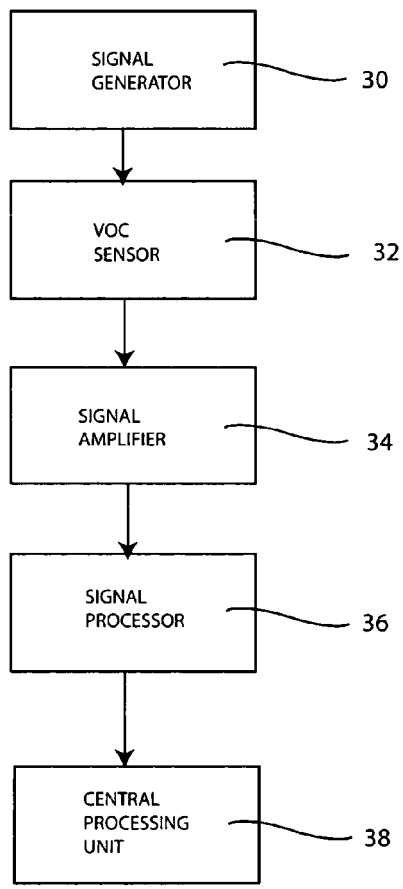
FIG. 4 shows the circuit design of FIGS. 1 and 2 as a flowchart.

FIGS. 3 and 4 show an electrical schematic and its complementary flowchart of the processing steps. The signal generator 30 supplies power to the volatile organic compound sensor 32 located either inside or outside a printer housing. A signal amplifier 34 takes the weak electrical pulse passed by the volatile organic compound sensor 32 and amplifies it for processing. The signal processor 36 interprets the electrical signal into data and assigns a value to the signal. An optional central processing unit 38 may contain a lookup table, an automatic disabling signal, or any other microprocessing software needed to utilize the data and cause the printer to perform the needed reaction.

Although specific materials, conditions, apparatus, components and ranges are used in the above disclosure and examples, that information is not intended to be limiting in the scope of the invention or the claims presented herein. One of ordinary skill in the art would be aware of alternatives and equivalents within the scope of the disclosed technology that could be used.

What is claimed:

1. A method of detecting a condition within a liquid electrophotographic printer comprising:
    providing a detector for volatile organic compounds within the printer;
    providing a signal when a predetermined level of volatile organic compounds is met or exceed within the printer; and
    wherein the detector identifies changes in electrical properties of a gas phase or gas stream within the printer to identify the predetermined level.

2. The method of claim 1 wherein the predetermined level is indicative of either an undesirable level of volatile organic compounds or an approach to an undesirable level of volatile organic compounds within the printer.

3. The method of claim 1, wherein the electrical property the detector measures is the dielectric constant of the gas phase or stream.

4. The method of claim 1 wherein the detector identifies the predetermined level of volatile organic compounds by absorption or adsorption of volatile organic Compounds onto a surface.

5. The method of claim 1, wherein the detector comprises two electrodes.

6. The method of claim 4 wherein the electrodes are positioned with a gap of between 0.01 and 0.25 inches apart.

7. The method of claim 1 wherein the frequency of the amplitude used is between about 0.05 and 10 MHz.

8. The method of claim 1 wherein more than one detector for volatile organic compounds is provided.

9. The method of claim 8 wherein the data received at each of the more than one detectors are averaged in a processing step.

10. A liquid electrophotographic printer having a detector for gas phase or gas stream volatile organic compounds within an area where a gas phase or gas stream passes from or remains in the printer and wherein the detector identifies changes in electrical properties of a gas phase or gas stream within the printer to identify a predetermined level of volatile organic compounds.

11. The printer of claim 10 wherein the detector is located within a housing of the printer.

12. The method of claim 10 wherein the frequency of the amplitude used is between about 0.05 and 10 MHz.

13. The printer of claim 10 wherein the detector comprises two electrodes.

14. The printer of claim 13, wherein the electrodes are space between 0.01 and 0.25 inches apart.

15. The printer of claim 10, wherein the electrical property being measured by the detector is the dielectric properties of the gas phase or stream.

16. The printer of claim 10 wherein the printer comprises more than one detector for gas phase or gas stream volatile organic compounds within at least one area where a gas phase or stream exits or remains in the printer.

* * * * *